(12) United States Patent
Weisel et al.

(10) Patent No.: US 11,246,586 B2
(45) Date of Patent: Feb. 15, 2022

(54) INSTRUMENT TO MANIPULATE AND PASS SUTURE

(71) Applicant: ARCH DAY DESIGN, LLC, Ventura, CA (US)

(72) Inventors: Thomas Weisel, Ventura, CA (US); Roger Pisarnwongs, Santa Clarita, CA (US)

(73) Assignee: ARCH DAY DESIGN, LLC, Ventura, CA (US)

( * ) Notice: Subject to any disclaimer, the term of this patent is extended or adjusted under 35 U.S.C. 154(b) by 0 days.

(21) Appl. No.: 16/898,246

(22) Filed: Jun. 10, 2020

(65) Prior Publication Data
US 2021/0052268 A1 Feb. 25, 2021

Related U.S. Application Data

(60) Provisional application No. 62/889,492, filed on Aug. 20, 2019.

(51) Int. Cl.
*A61B 17/04* (2006.01)
(52) U.S. Cl.
CPC ...... *A61B 17/0469* (2013.01); *A61B 17/0482* (2013.01)
(58) Field of Classification Search
CPC ............ A61B 17/0469; A61B 17/0482; A61B 17/0483; A61B 17/0485; A61B 17/06004; A61B 17/29; A61B 2017/00349; A61B 2017/06009; A61B 2017/06014; A61B 2017/06019
See application file for complete search history.

(56) References Cited

U.S. PATENT DOCUMENTS

| 2,850,803 | A | | 9/1958 | Briskman et al. |
| 3,879,813 | A | | 4/1975 | Shadwell |
| 5,059,201 | A | * | 10/1991 | Asnis ..................... A61B 17/04 606/144 |

(Continued)

FOREIGN PATENT DOCUMENTS

| WO | 2006023975 A2 | 3/2006 |
| WO | 2012093094 A1 | 7/2012 |

OTHER PUBLICATIONS

Arthroscopic TAG Suture Anchors—1998 Smith and Nephew product catalog.

(Continued)

*Primary Examiner* — Dianne Dornbusch
(74) *Attorney, Agent, or Firm* — Innovation Capital Law Group, LLP; Vic Lin

(57) ABSTRACT

A surgical instrument can manipulate and pass suture through tissue. The device can easily pass suture through tissue with the suture fixed to the mechanism or where the suture is captured by the mechanism and allowed to slide. Along with this ability to control suture in one of two ways is a feature to provide a large amount of suture on the other side of the tissue that will be relatively easy for the surgeon to grab and pull out of the arthroscopic portal. The device includes a handle with a hollow shaft extending therefrom and a set of fingers movable into and out of the shaft. The fingers can be designed to capture suture, permit the suture to slide while captured, and optionally hold the suture in the device.

21 Claims, 13 Drawing Sheets

(56) References Cited

U.S. PATENT DOCUMENTS

| | | | |
|---|---|---|---|
| 5,222,977 A * | 6/1993 | Esser | A61B 17/0469 |
| | | | 606/144 |
| 5,250,053 A | 10/1993 | Snyder | |
| 5,261,917 A | 11/1993 | Hasson et al. | |
| 5,279,311 A | 1/1994 | Snyder | |
| 5,312,432 A | 5/1994 | Pingleton et al. | |
| 5,318,589 A | 6/1994 | Lichtman | |
| 5,342,389 A | 8/1994 | Haber et al. | |
| 5,454,822 A | 10/1995 | Schob et al. | |
| 5,499,991 A | 3/1996 | Garman et al. | |
| 5,632,751 A | 5/1997 | Piraka | |
| 5,653,716 A | 8/1997 | Malo et al. | |
| 5,782,747 A | 7/1998 | Zimmon | |
| 5,797,958 A | 8/1998 | Yoon | |
| 5,817,111 A * | 10/1998 | Riza | A61B 17/06109 |
| | | | 606/148 |
| 5,910,148 A | 6/1999 | Reimels et al. | |
| 5,984,938 A | 11/1999 | Yoon | |
| 5,993,466 A | 11/1999 | Yoon | |
| 6,022,360 A | 2/2000 | Reimels et al. | |
| 6,616,683 B1 | 9/2003 | Toth et al. | |
| 7,169,156 B2 | 1/2007 | Hart | |
| 7,261,725 B2 | 8/2007 | Binmoeller | |
| 7,766,937 B2 | 8/2010 | Ravikumar | |
| 8,066,718 B2 | 11/2011 | Weisel et al. | |
| 8,133,255 B2 | 3/2012 | Ravikumar | |
| 8,496,656 B2 | 7/2013 | Shields et al. | |
| 8,585,714 B2 | 11/2013 | Weisel et al. | |
| 9,931,114 B2 | 4/2018 | Stewart et al. | |
| 9,936,943 B1 | 4/2018 | Mancini et al. | |
| 10,420,574 B2 | 9/2019 | Thrasher, III | |
| 11,096,682 B2 | 8/2021 | Foerster et al. | |
| 2002/0183785 A1 | 12/2002 | Howell et al. | |
| 2004/0055608 A1 | 3/2004 | Stevens et al. | |
| 2004/0087967 A1 | 5/2004 | Schur et al. | |
| 2004/0172057 A1 | 9/2004 | Guillebon et al. | |
| 2004/0249393 A1 | 12/2004 | Weisel et al. | |
| 2007/0213767 A1 | 9/2007 | Ravikumar | |
| 2007/0250112 A1 | 10/2007 | Ravikumar et al. | |
| 2009/0062819 A1 * | 3/2009 | Burkhart | A61B 17/0469 |
| | | | 606/148 |
| 2010/0262181 A1 | 10/2010 | Choi et al. | |
| 2011/0071550 A1 | 3/2011 | Diduch et al. | |
| 2012/0123448 A1 * | 5/2012 | Flom | A61B 17/0483 |
| | | | 606/144 |
| 2012/0143222 A1 | 6/2012 | Dravis et al. | |
| 2013/0030450 A1 | 1/2013 | Dreyfuss et al. | |
| 2013/0030462 A1 | 1/2013 | Keating et al. | |
| 2013/0116709 A1 | 5/2013 | Ziniti et al. | |
| 2013/0144315 A1 | 6/2013 | Hart et al. | |
| 2013/0190782 A1 | 7/2013 | Nason | |
| 2013/0218175 A1 | 8/2013 | Auerbach et al. | |
| 2013/0324803 A1 | 12/2013 | Mohajer | |
| 2014/0012292 A1 | 1/2014 | Stewart et al. | |
| 2014/0222033 A1 * | 8/2014 | Foerster | A61B 17/0483 |
| | | | 606/144 |
| 2015/0094739 A1 * | 4/2015 | Norton | A61B 17/0483 |
| | | | 606/144 |
| 2015/0112368 A1 | 4/2015 | Stewart et al. | |
| 2015/0272603 A1 | 10/2015 | Shelton, IV et al. | |
| 2016/0000423 A1 | 1/2016 | Shields et al. | |
| 2016/0022488 A1 | 1/2016 | Dimmig et al. | |
| 2016/0166248 A1 | 6/2016 | Deville et al. | |
| 2016/0278801 A1 | 9/2016 | Michelini et al. | |
| 2017/0042533 A1 * | 2/2017 | Lunn | A61B 17/0483 |
| 2017/0049465 A1 | 2/2017 | Ravikumar et al. | |
| 2017/0367693 A1 | 12/2017 | Heneveld | |
| 2018/0116652 A1 | 5/2018 | Torrie | |
| 2019/0125384 A1 | 5/2019 | Scheib et al. | |
| 2019/0336124 A1 | 11/2019 | Pisarnwongs et al. | |

OTHER PUBLICATIONS

Blitz Suture Retriever, Linvatec, 1995 product catalog.
International Search Report dated Jul. 10, 2019 from PCT Application No. PCT/US2019/030221.
SutureLasso—2003 Arthrex catalog, Shoulder Arthroscopy & Mini-Open Repairs, 10-21.
International Preliminary Report on Patentability (Chapter II) dated Feb. 2, 2021 from PCT Application No. PCT/US2020/070307.
International Preliminary Report on Patentability dated Mar. 2, 2021 from PCT Application No. PCT/US2020/045998.
International Search Report & Written Opinion dated Nov. 23, 2020 from PCT Application No. PCT/US20/45998.
International Search Report & Written Opinion dated Oct. 9, 2020 from PCT Application No. PCT/US2020/070307.
International Search Report & Written Opinion dated Dec. 14, 2021 from PCT Application No. PCT/US21/49936.

* cited by examiner

INSTRUMENT TO MANIPULATE AND PASS SUTURE

CROSS-REFERENCE TO RELATED APPLICATIONS

This application claims the benefit of priority of U.S. provisional patent application No. 62/889,492, filed Aug. 20, 2019, the contents of which are herein incorporated by reference.

BACKGROUND OF THE INVENTION

1. Field of the Invention

Embodiments of the invention relate generally to surgical instruments. More particularly, embodiments of the invention relate to surgical instruments that can manipulate and pass suture through tissue.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Often times an important aspect of a surgical procedure is to pass suture through tissue. This could be required to mend a tear or connect two or more pieces of soft tissue. Though this task is common, it can be challenging for the surgeon especially in an arthroscopic procedure where visualization is limited.

Many devices have been created to address difficult suturing scenarios but there are still certain procedures and anatomies where the average surgeon still struggles. For example, suturing the labrum at times can prove challenging particularly when the tissue is severely damaged. In such cases decreasing the overall profile of the needle penetrating the tissue and optimizing the working profile of the instrument to improve access to the working site can be critical factors to facilitate suturing.

Within this smaller needle profile, a mechanism must be housed that allows easy passing and retrieving of suture by the doctor in an arthroscopic atmosphere. With many devices currently on the market, the mechanism can grab suture and hold it fixed but there are certain surgical techniques that require the suture to be captured and allowed to slide within the mechanism.

In view of the foregoing, there is a need for a device that easily passes suture through tissue with the suture fixed to the mechanism or where the suture is captured by the mechanism and allowed to slide. Along with this ability to control suture in one of two ways is a feature to provide a large amount of suture on the other side of the tissue that will be relatively easy for the surgeon to grab and pull out of the arthroscopic portal. This system must also be relatively simple so that the manufacturing cost can be kept at a reasonable level.

SUMMARY OF THE INVENTION

Embodiments of the present invention provide a medical instrument comprising a handle; a hollow shaft extending from the handle; a set of fingers including a first finger and a second finger; and a slide disposed on the handle, the slide operably connected to the set of fingers to cause the set of fingers to extend from the hollow shaft, in a deployed configuration, and retract into the hollow shaft, in a retracted configuration, upon movement of the slide along the handle, wherein the first finger and the second finger separating from each other, resulting in an open configuration, as the set of fingers move from the retracted configuration to the deployed configuration; and the first finger and the second finger coming together, resulting in a closed configuration, at a joint as the set of fingers move from the deployed configuration to the retracted configuration.

Embodiments of the present invention further provide a medical instrument comprising a handle; a hollow shaft extending from the handle, the hollow shaft having a distal end with a sharpened tip; a set of fingers including a short finger and a hooked finger having a hook at a hooked finger distal end thereof, a hook distal end surface of the hook facing the handle, a short finger distal end surface facing the hook distal end surface; and a slide disposed on the handle, the slide operably connected to the set of fingers to cause the set of fingers to extend from the hollow shaft, in a deployed configuration, and retract into the hollow shaft, in a retracted configuration, upon movement of the slide along the handle, wherein the short finger and the hooked finger separating from each other, resulting in an open configuration, as the set of fingers move from the retracted configuration to the deployed configuration; the first finger and the second finger coming together, resulting in a closed configuration, at a joint as the set of fingers move from the deployed configuration to the retracted configuration; and a slot is formed between the short finger and the hooked finger in the closed configuration.

Embodiments of the present invention also provide a method for capturing a suture comprising inserting a tip of a medical instrument through tissue having the suture thereunder, the medical instrument comprising a handle; a hollow shaft extending from the handle; a set of fingers including a first finger and a second finger; and a slide disposed on the handle, the slide operably connected to the set of fingers to cause the set of fingers to extend from the hollow shaft, in a deployed configuration, and retract into the hollow shaft, in a retracted configuration, upon movement of the slide along the handle, wherein the first finger and the second finger separating from each other, resulting in an open configuration, as the set of fingers move from the retracted configuration to the deployed configuration; and the first finger and the second finger coming together, resulting in a closed configuration, at a joint as the set of fingers move from the deployed configuration to the retracted configuration; moving the slide to move the set of fingers into the open configuration and deployed configuration; capturing the suture in the slot; moving the slide to move the set of fingers into the closed configuration and the retracted configuration; and withdrawing the medical instrument from the tissue.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

Figure 1:
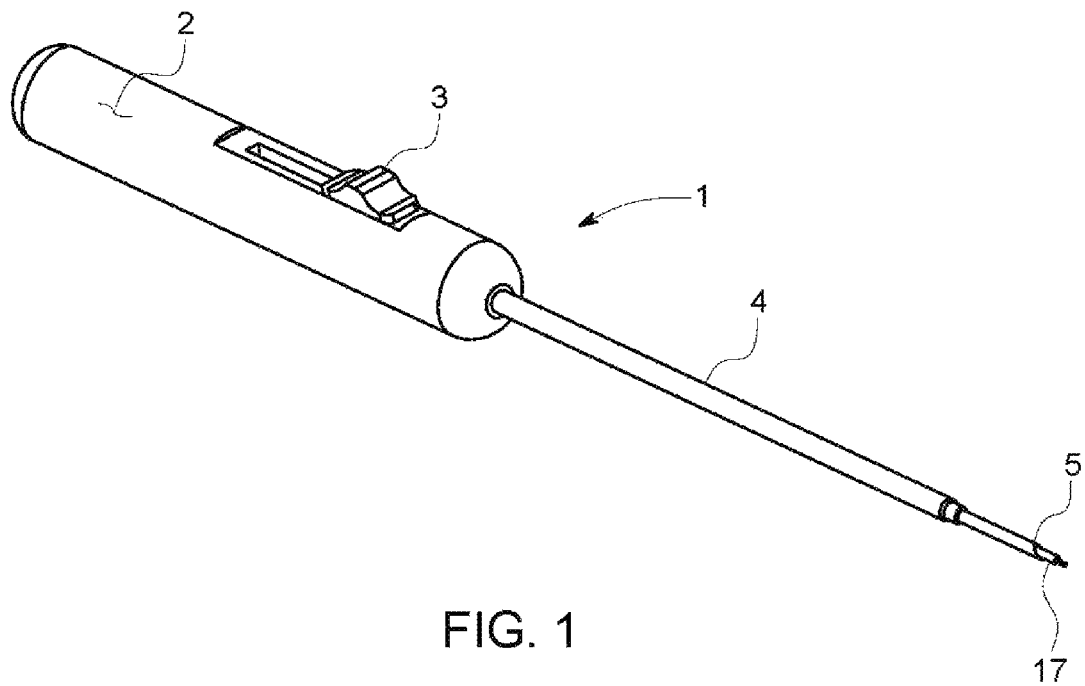
FIG. 1 illustrates a perspective view of an instrument according to an exemplary embodiment of the present invention.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

As is well known to those skilled in the art, many careful considerations and compromises typically must be made when designing for the optimal configuration of a commercial implementation of any system, and in particular, the embodiments of the present invention. A commercial implementation in accordance with the spirit and teachings of the present invention may be configured according to the needs of the particular application, whereby any aspect(s), feature (s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Broadly, embodiments of the present invention provide a surgical instrument that can manipulate and pass suture through tissue. The device can easily pass suture through tissue with the suture fixed to the mechanism or where the suture is captured by the mechanism and allowed to slide. Along with this ability to control suture in one of two ways is a feature to provide a large amount of suture on the other side of the tissue that will be relatively easy for the surgeon to grab and pull out of the arthroscopic portal. The device includes a handle with a hollow shaft extending therefrom and a set of fingers movable into and out of the shaft. The fingers can be designed to capture suture, permit the suture to slide while captured, and optionally hold the suture in the device.

Referring now to FIG. 1, a device 1, also referred to as instrument 1, includes a handle 2 attached to a shaft 4 with a distal working end 5. A slide 3 is disposed within the handle 2 with a portion of the slide 3 accessible from an exterior of the handle. The slide 3 can be used to control a set of fingers 17 that can be used to manipulate suture.

Figure 2:
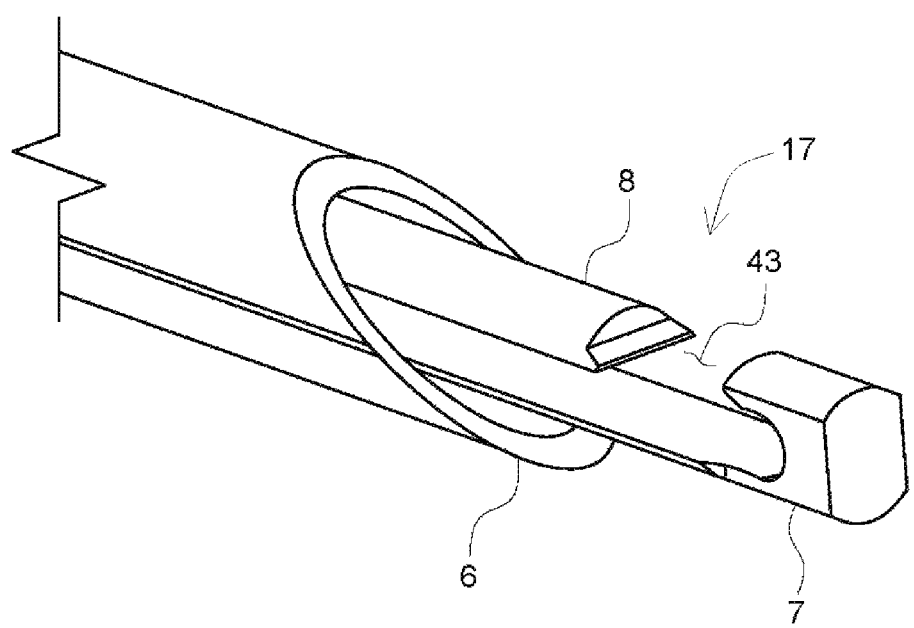
FIG. 2 illustrates a detailed perspective view of a distal end of the instrument of FIG. 1 in an open configuration.
Figure 3:
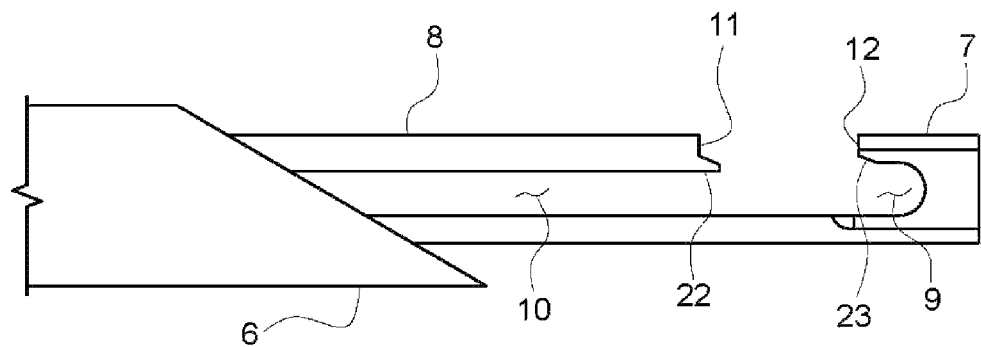
FIG. 3 illustrates a detailed side view of the distal end of FIG. 2.

Referring also to FIGS. 2 and 3, a close-up of the distal end of the device 1 is shown. The shaft 4 can be formed as a hollow cannula similar to a needle. While the Figures show a generally linear hollow cannula, it should be understood that the shaft 4 may include one or more bends therealong, including near its distal working end 5, depending on the particular application. A sharpened tip 6 of the shaft 4 can enhance the ability of the shaft 4 to pierce or slide around tissue. The set of fingers 17, shown in FIG. 2 in a deployed, open configuration, can extend into and out of the shaft 4. The set of fingers 17 can include a short finger 8 and a hooked finger 7. These can be positioned relative to each other with a gap 43 as shown in FIG. 2 or can be pushed together with the aid of an active (e.g., secondary slide in handle) or passive (e.g., spring) actuation mechanism.

Figure 4A:
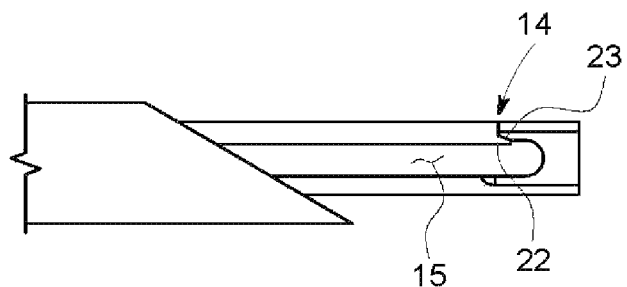
FIG. 4A illustrates a detailed side view of the distal end of FIG. 2 in a closed configuration.
Figure 4B:
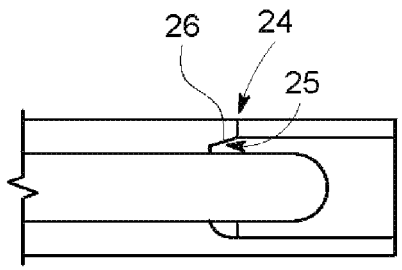
FIG. 4B illustrates a detailed side view of an alternate configuration of the distal end.

A slot 15 can be produced when the short finger 8 and the hooked finger 7 are brought together as shown in FIG. 4A. The connection can be a butt joint or can have added features, as illustrated, to lock the two fingers together. In the illustrated example of FIGS. 3 and 4A, a distal end 11 of the short finger 8 has a tooth 22 that meshes with a chamfer 23 of a proximal portion 12 of the hooked finger 7. When the features are brought together, as shown in FIG. 4A, the joint 14 is created. The tooth 22 in this example is held from moving radially outward by the hooked finger's chamfer 23 and vice versa. FIG. 4B is similar except the connection scheme is reversed with features tooth 22 and chamfer 23 being replaced with short finger feature 26 and hooked finger feature 25 respectively to form a joint 24.

Figure 5:
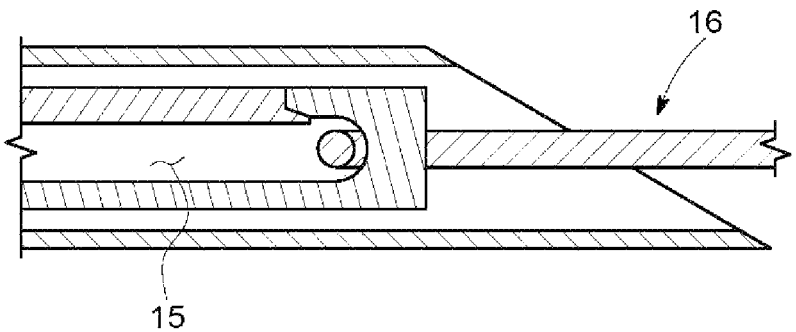
FIG. 5 illustrates a cross-sectional detailed side view of a suture captured in the formed slot of the instrument of FIG. 1.
Figure 6:
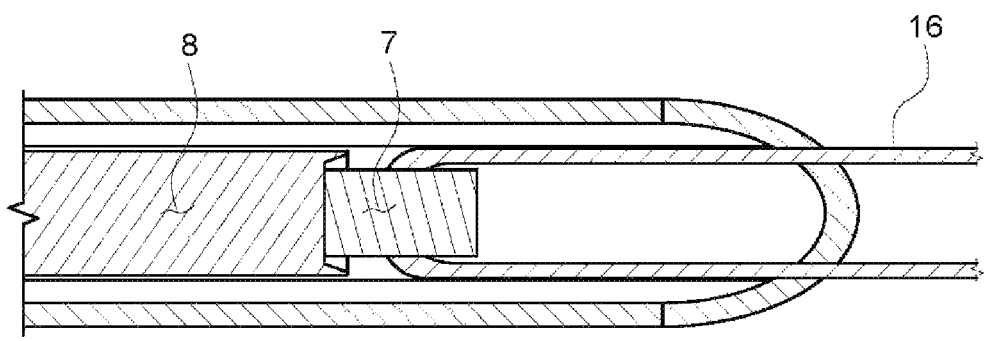
FIG. 6 illustrates a cross-sectional top view of the suture captured as shown in FIG. 5.
Figure 7:
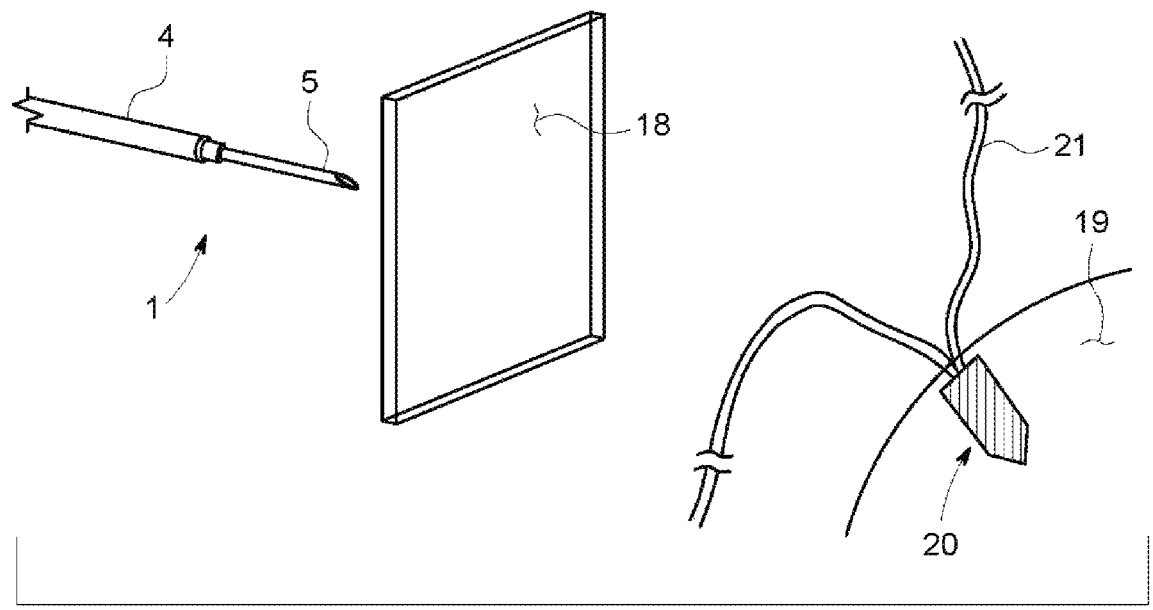
FIG. 7 illustrates a step in the use of the instrument of FIG. 1 in retrieving suture end extending from an anchor.
Figure 8:
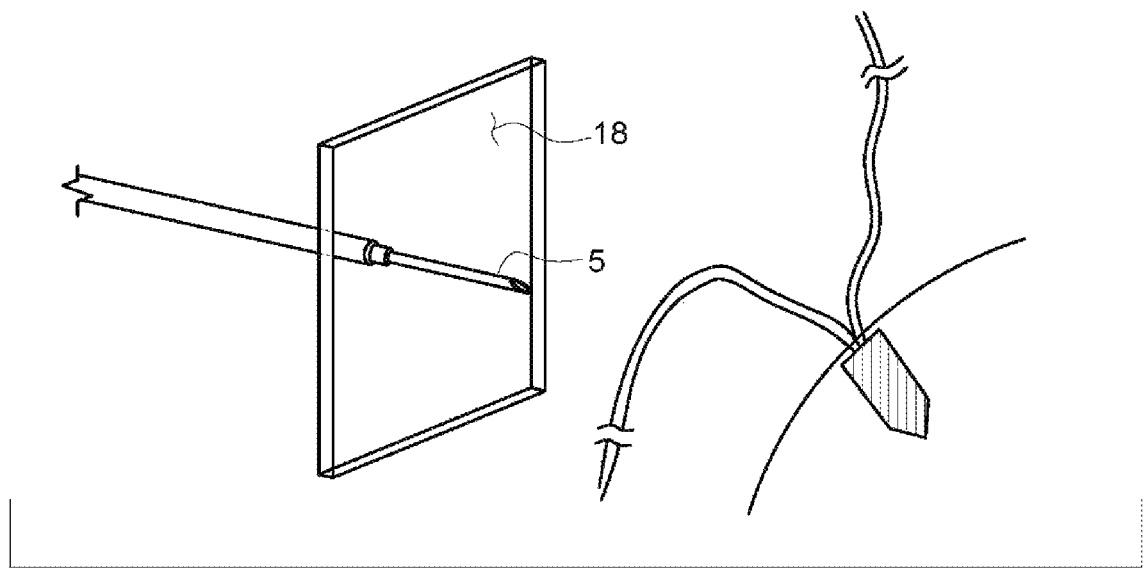
FIG. 8 illustrates the instrument of FIG. 1 passing through tissue.

Referring also to FIGS. 5 and 6, the formed slot 15 can be sized such that if a suture 16 is captured it has ample room to allow the suture 16 to slide while being retained within the slot 15.

Referring further to FIGS. 7 through 12, an example of an exemplary use of the device 1 is illustrated. An anchor 20, also referred to as an implant 20, can be placed in bone 19. A strand of suture 21 can be attached to the anchor 20. Though the suture 21 can be loosely attached to the anchor 20 (allowed to slide), in this case the suture 21 is fixed to the anchor 20.

Figure 9:
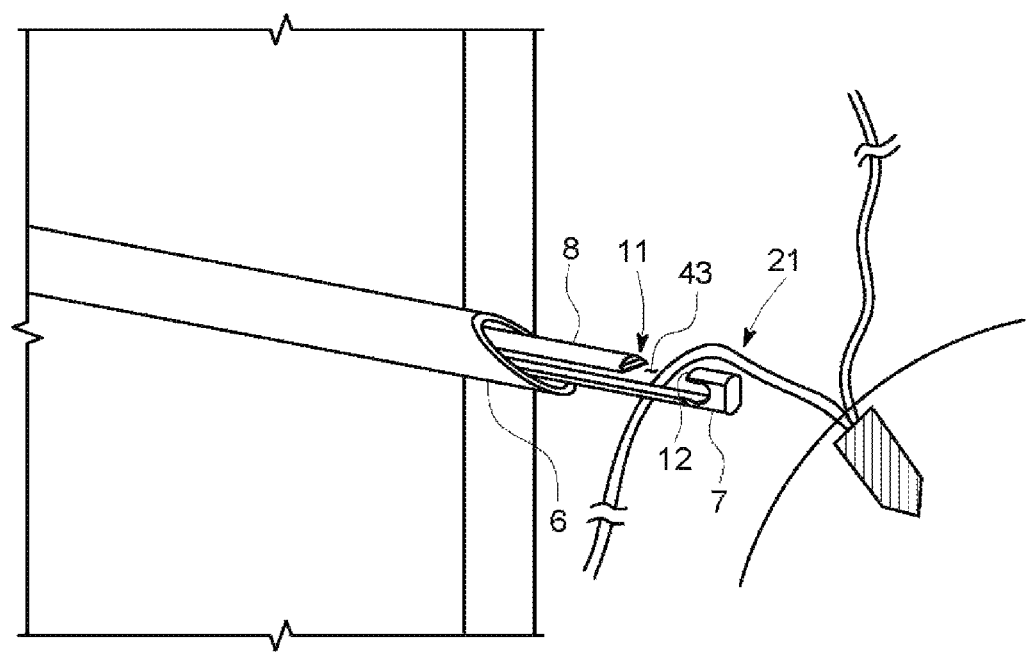
FIG. 9 illustrates the distal end of the instrument of FIG. 1 in an open configuration to retrieve suture in the slot formed therein.
Figure 10:
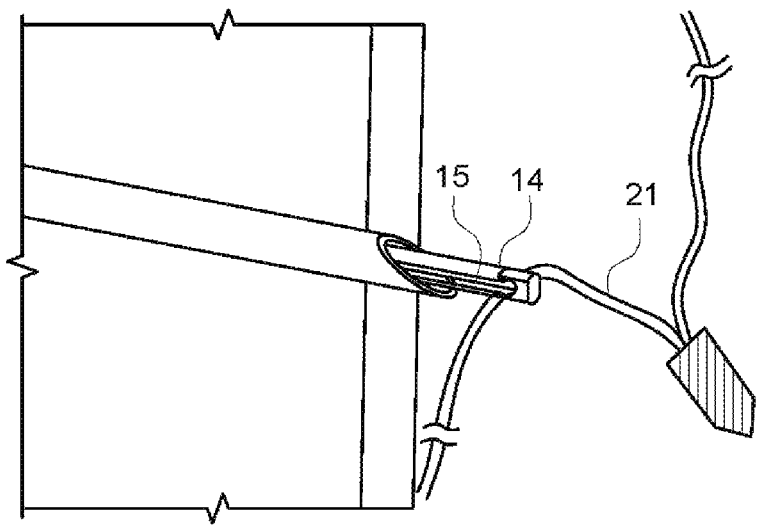
FIG. 10 illustrates closure of the slot in the distal end of the instrument of FIG. 1.
Figure 11:
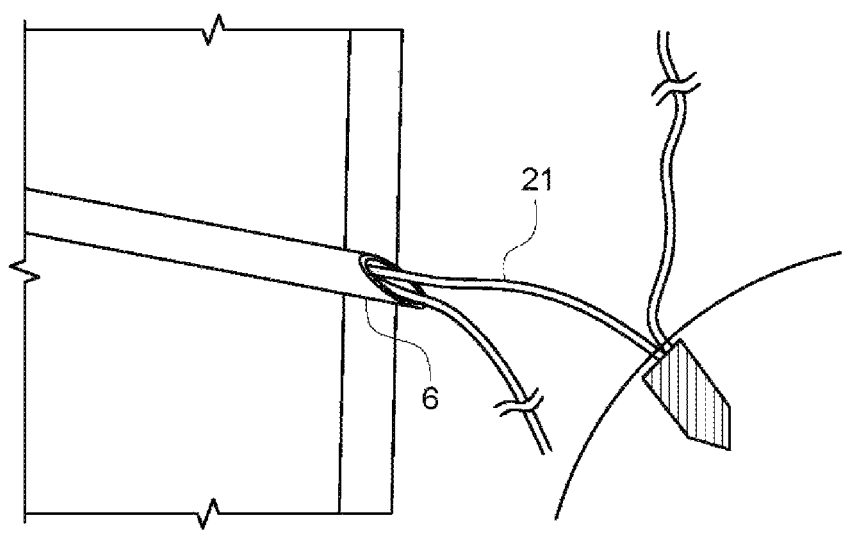
FIG. 11 illustrates the distal end of the slot and the suture being withdrawn into the distal end tip of the instrument of FIG. 1.
Figure 12:
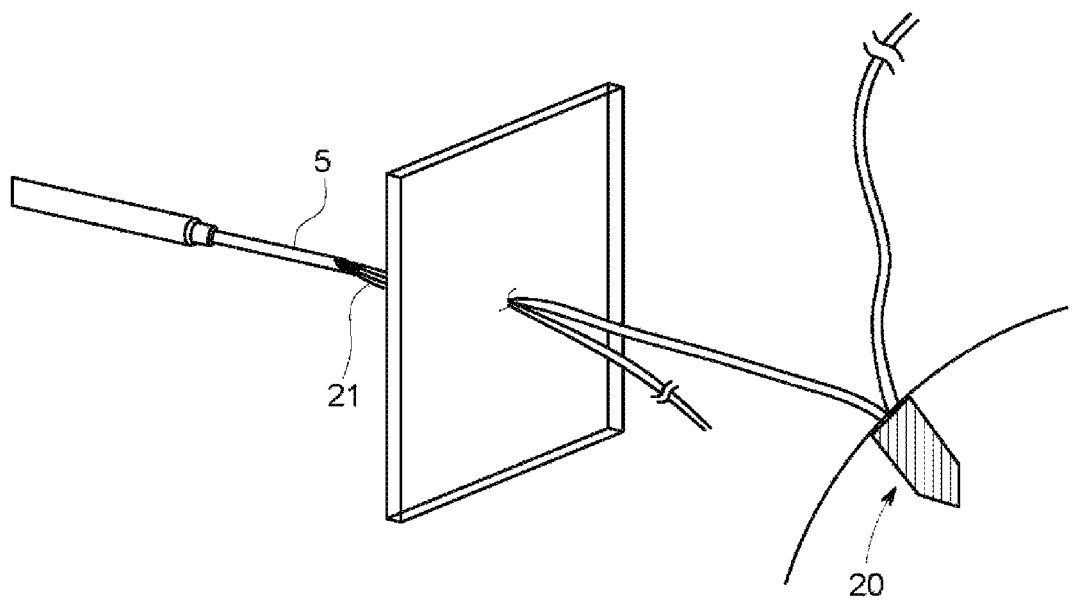
FIG. 12 illustrates the instrument of FIG. 1 and the suture being pulled through the tissue.

The goal for this example is to pull one of the strands of the suture 21 through the tissue 18. This can be done by piercing the distal working end 5 through the tissue 18 with the set of fingers 17 in a retracted configuration, inside the shaft 4, so that the sharpened tip 6 can aid in the penetration of the tissue 18. The short finger 8 and the hooked finger 7 can then be deployed out of the shaft 4, as illustrated in FIG. 9, to the point that a gap 43 is opened between the short finger 8 and the hooked finger 7. The suture 21 can be guided into the gap 43 and the distal end 11 of the short finger and the proximal portion 12 of the hooked finger 7 can be brought together such that the suture 21 is now captured within the slot 15. The short finger 8 and the hooked finger 7, along with the captured suture 21 can be pulled slightly into the needle 6, as shown in FIG. 11. As the device 1 is removed from the tissue 18, the leg of the suture 21 attached to the anchor 20 can be held fixed so the suture 21 can slide through the slot 15 in order to allow device 1 to pull away from the implant 20. Once the operation is done, the short finger 8 and the hooked finger 7 can be deployed again and the suture 21 is released from the slot 15 via the gap 43.

Figure 13:
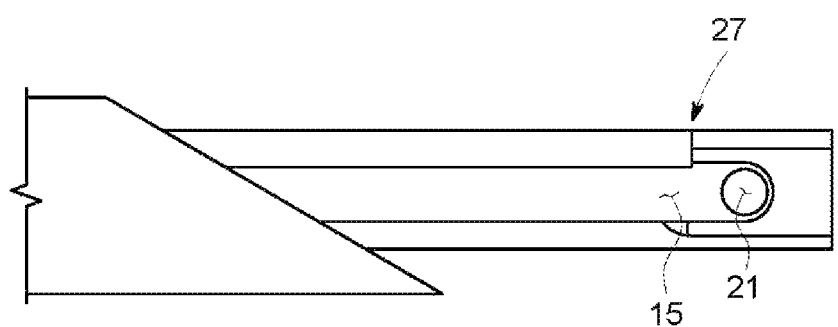
FIG. 13 illustrates a detailed side view of a distal end of an instrument according to an embodiment of the present invention.
Figure 14:
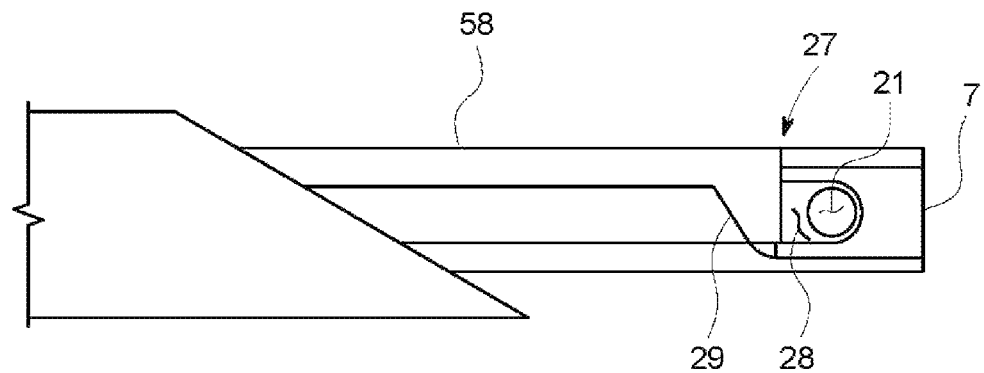
FIG. 14 illustrates a detailed side view of a distal end of an instrument according to an embodiment of the present invention.
Figure 15:
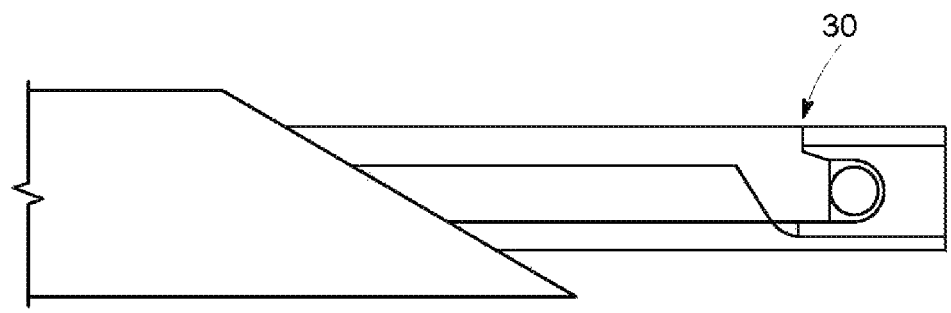
FIG. 15 illustrates a detailed side view of a distal end of an instrument according to an embodiment of the present invention.

Referring now to FIGS. 13 through 15, variations of the mating scheme between the short finger 8 and the hooked finger 7 are illustrated. A simple butt joint 27 is shown in FIG. 13 with the created slot 15. The suture 21 is shown in a distal position as if the device is being removed from the tissue and the suture 21 is permitted to slide in slot 15. The short finger 8 and the hooked finger 7 are unable to separate outward because the inside diameter of the shaft 4 contains them. In FIG. 14, a ram 29 is added to the short finger 8 in order to mate more closely with the hooked finger 7 and make the construct more stable. The size of the slot 28 is also minimized, adding axial control of the suture 21 while still allowing the suture 21 to slide in the slot 28. FIG. 15 shows a design combining the features of FIGS. 14 and 4A, where a ram 29 extends partially into the slot 28 (not labelled in FIG. 15 but shown in FIG. 14). In the design of FIG. 15, the ram 29 may extend into the slot 28 to secure the suture in a non-sliding position at the end of the ram 29. Further, in some embodiments, a tapered lead-in may be provided on the ram 29 to meet with a mating taper of the hooked finger 7, thus guiding the short finger 8 and the hooked finger 7 together in a secure position.

Figure 16:
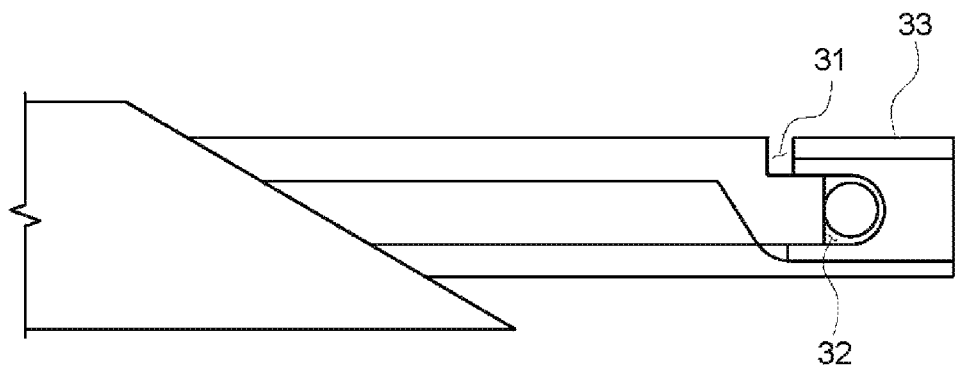
FIG. 16 illustrates a detailed side view of a distal end of an instrument with a suture capturing ram according to an embodiment of the present invention.
Figure 17:
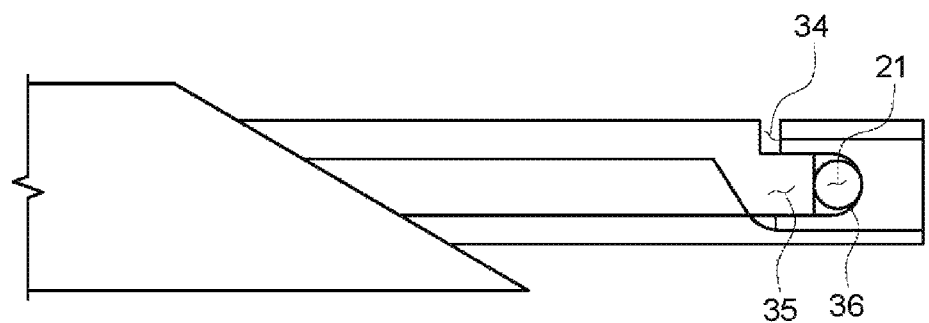
FIG. 17 illustrates a detailed side view of a distal end of an instrument with the suture capturing ram of FIG. 16 pressing to hold the suture according to an embodiment of the present invention.

Referring now to FIGS. 16 and 17 a design with additional features is shown. With the fingers positioned relative to each other, with a space 31 between the short finger 8 and the hooked finger 7, as shown in FIG. 16, a slot 32 is created such that the suture 21 is allowed to slide. If holding the suture 21 fixed between the fingers is desired, then the fingers can be brought closer together, resulting in a smaller space 34, as shown in FIG. 17, thus allowing ram 35 to pinch the suture 21 against wall 36 of the hooked finger 7.

Figure 18:
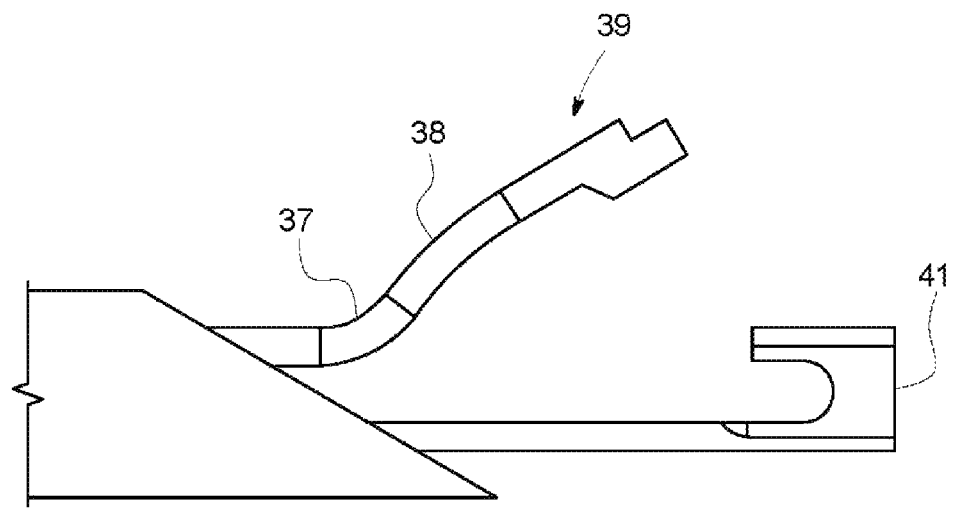
FIG. 18 illustrates a detailed side view of a distal end of an instrument with a bend in the short finger according to an embodiment of the present invention.

FIG. 18 presents a variation of the short finger 39 by adding one or more bends, such as proximate bend 37 and distal bend 38, for example. The bends allows a larger opening and movable finger for easier suture capturing. Bends can also be imparted on the hooked finger 41 in unison or alone.

Figure 19:
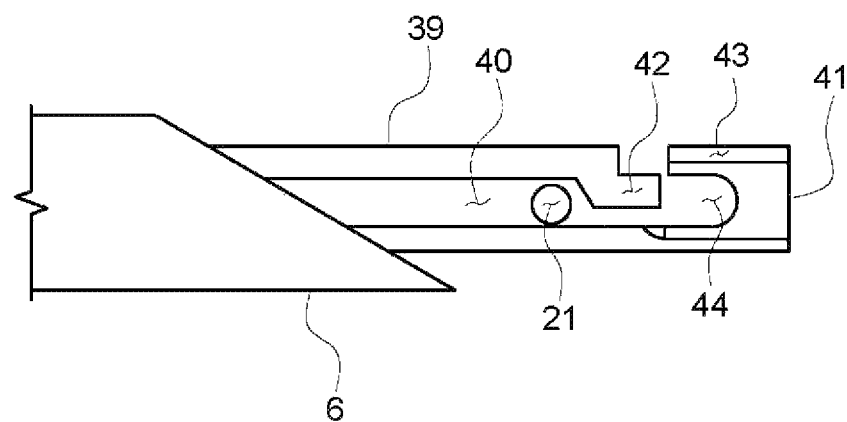
FIG. 19 illustrates a detailed side view of a distal end of an instrument with a suture captured in a slot under the short finger according to an embodiment of the present invention.
Figure 20:
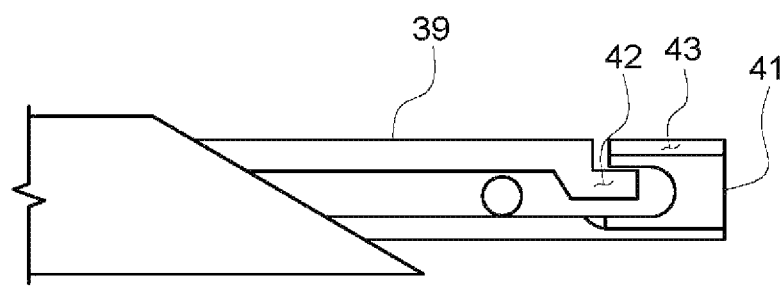
FIG. 20 illustrates the instrument of FIG. 19 in a closed configuration.
Figure 21:
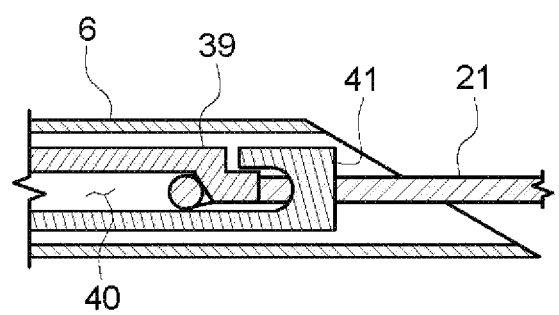
FIG. 21 illustrates the instrument of FIG. 19 in a fully retracted configuration.
Figure 22:
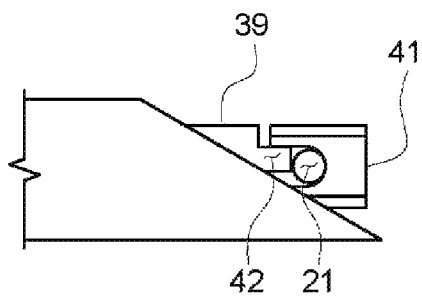
FIG. 22 illustrates the instrument of FIG. 19 with the suture captured between the end of the short finger and the end of the long finger.

FIG. 19 illustrates the fingers have been retracted enough that the short finger 39 and the hooked finger 41 have captured the suture 21 in slot 40. In FIG. 20 the fingers 39, 41 are brought even closer such that a short finger ledge 42 goes under a hooked finger ledge 43 to create a connection between the two fingers 39, 41. The suture 21 is able to slide even if pulled into the shaft 4 a bit as shown in FIG. 21. If the fingers 39, 41 are retracted far enough into the shaft 4, friction may restrict the sliding motion of the suture 21 and act as a non-sliding hold. A resultant variation of this method when, combined with the description of FIGS. 16 and 17, is shown on FIG. 22.

Figure 23:
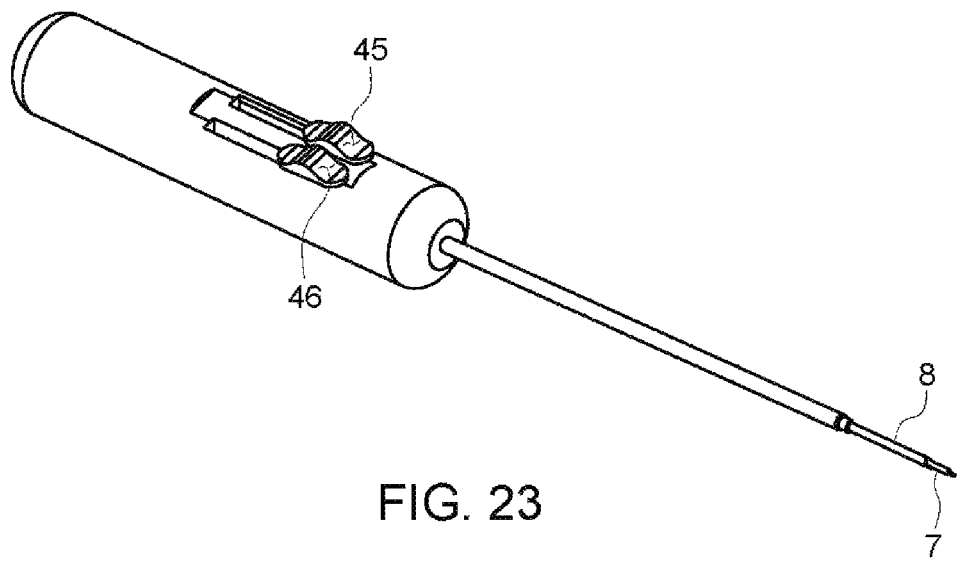
FIG. 23 illustrates an instrument with dual controls according to an exemplary embodiment of the present invention.
Figure 24:
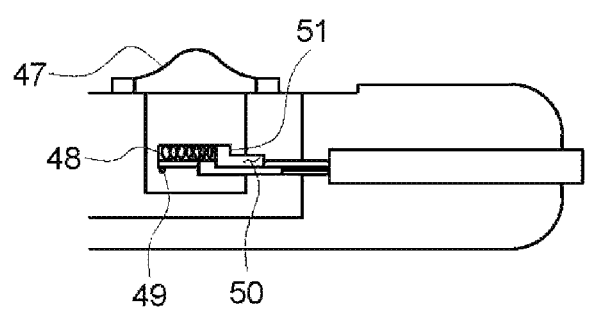
FIG. 24 illustrates a connection mechanism for the slide controls.
Figure 25:
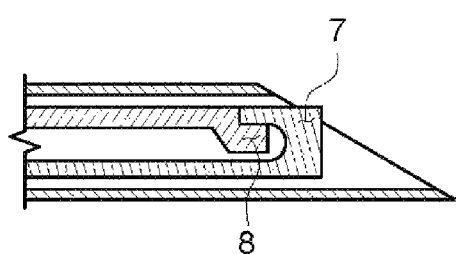
FIG. 25 illustrates a cross-sectional view of an end of the instrument according to an embodiment of the present invention.
Figure 26:
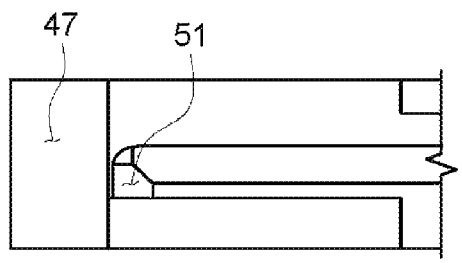
FIGS. 26 through 29 illustrate methods for connecting the slide controls with the fingers of the instrument.
Figure 27:
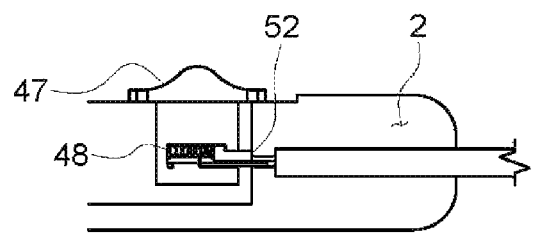
Figure 28:
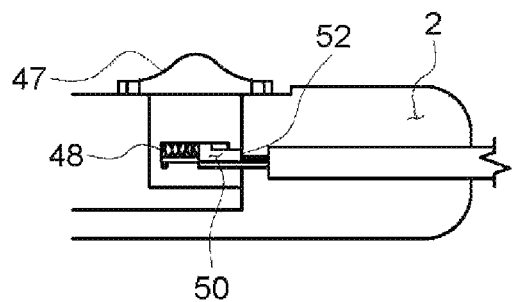

To actuate the movement of the short finger relative to the hooked finger, several methods can be used. One would be to have two separate slide mechanisms, each attached to one of the fingers, as shown in FIG. 23. Slide 45 can be attached to the short finger 8 and a second slide 46 can be attached to the hooked finger 7 or vice versa. This allows the two fingers 8, 7 to be controlled independently.

Figure 29:
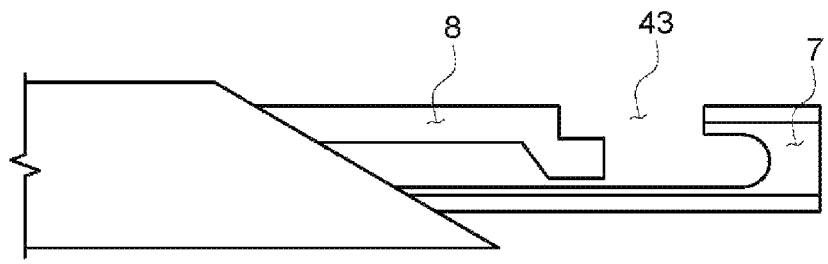

FIGS. 24 through 29 show one method of attaching a finger to a slide using an L-bend 51 and a cross hole 49 in the slide. In this case both fingers 7 and 8 are attached to a single slide 47. The hooked finger 7 can be fixed to the slide using an L-bend 51 while the short finger 8 can be allowed to travel axially within the slide 47 through an L-block 50. In the relaxed state, the fingers are biased together or closed (see FIG. 25) using spring 48 and stop 52 in the slide. When the slide assembly is actuated distally, the L-block 50 hits stop 52 in the handle 2 and prevents the short finger 8 from advancing relative to the hooked finger 7. The slide 47 continues advancing along with the hooked finger 7, creating an opening 43 between the fingers as shown in FIG. 29.

A third method could use a spring and stop on each finger so that, in the relaxed state, the fingers are configured as in FIG. 2. However, with one slide the user can retract the hooked finger 7 until it comes in contact with the short finger 8 then both are retracted together.

Figure 30:
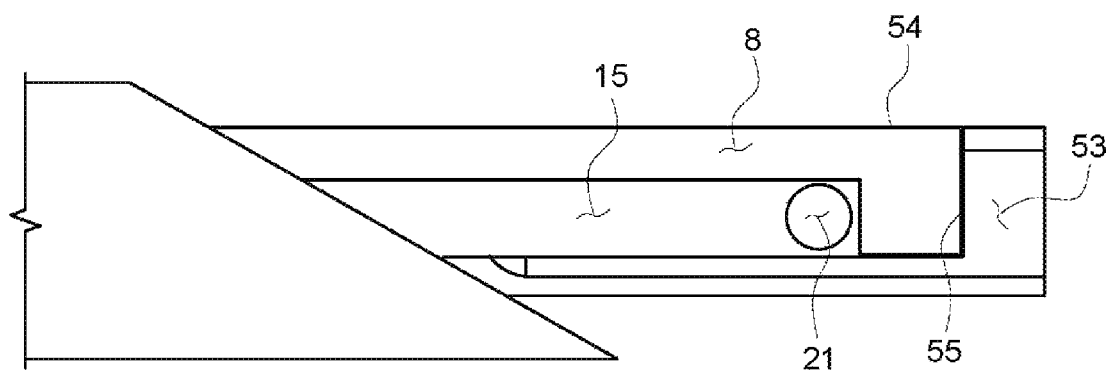
FIGS. 30 through 32 illustrate various structures for the interaction between the short and long fingers of the instrument, with the short finger being the upper finger.
Figure 31:
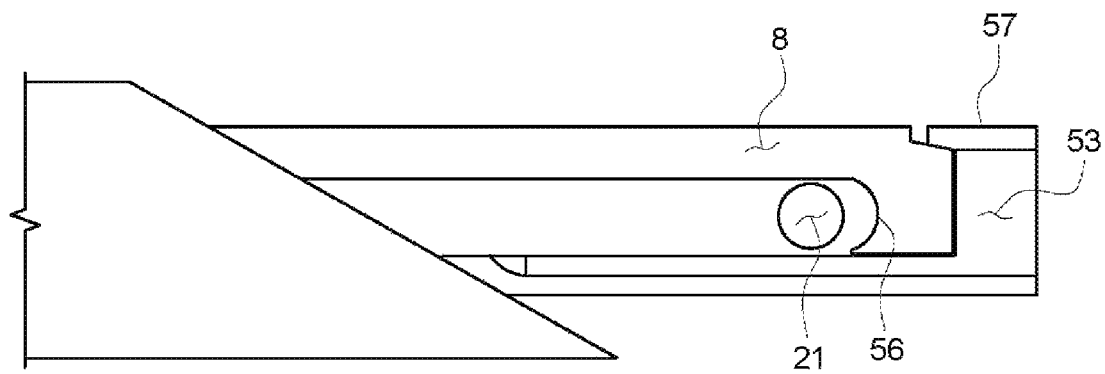
Figure 32:
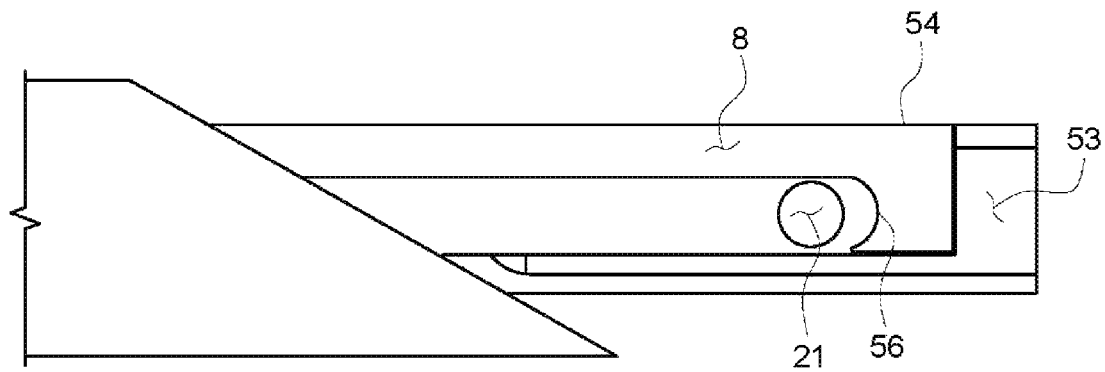

FIGS. 30 through 32 show variations with the short finger 8 positioned as the upper finger. FIG. 30 shows one potential variation without a hook. The short finger 8 and long finger 53 join together using simple butt joint 54 forming a slot 15 to capture suture 21. FIG. 31 shows a configuration with a hook 56 on the short finger 8. The long finger 53 includes locking tooth 57 which temporarily locks the two fingers together. FIG. 32 shows a configuration with a hook 56 on the short finger 8, but in this case the two fingers are held together using a simple butt joint.

Figure 33:
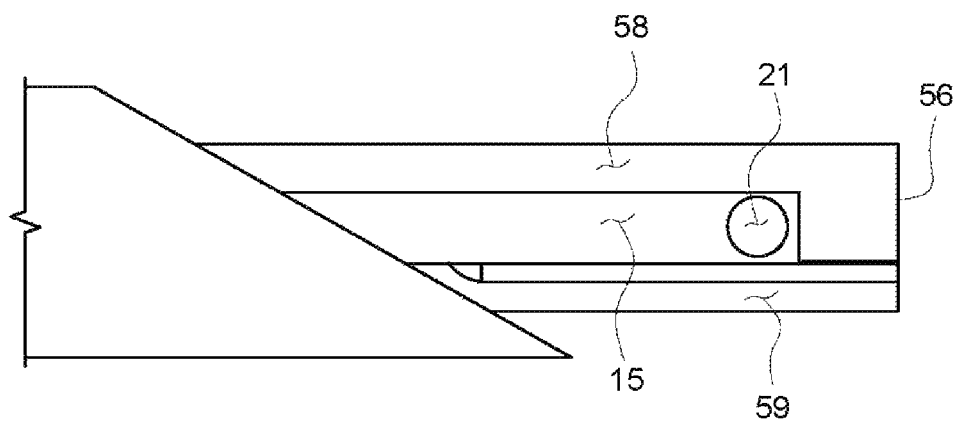
FIG. 33 illustrates a structure for the interaction between the short and long fingers where both fingers are approximately the same length.

FIG. 33 shows a variation in which the two fingers are of nearly equal length. An upper finger 58 includes a head 56 while the lower finger 59 can be a simple straight wire or ribbon. The two fingers 58, 56 can come together to form slot 15 which is used to contain the suture 21.

Figure 34:
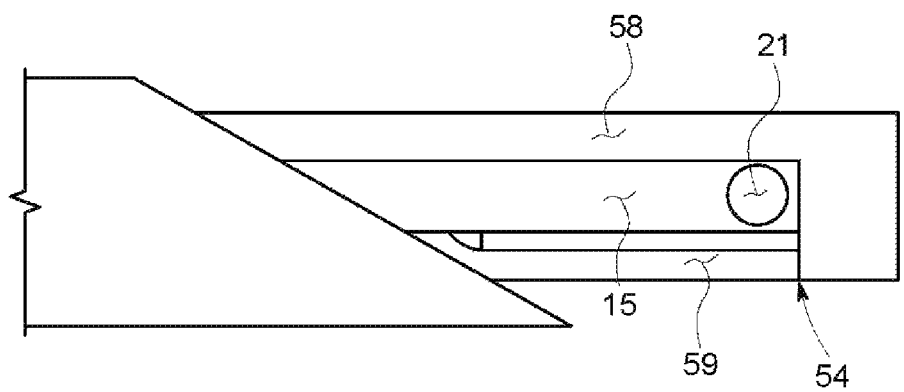
FIGS. 34 and 35 illustrate a structure for the interaction between the short and long fingers of the instrument, with the long finger being the upper finger.
Figure 35:
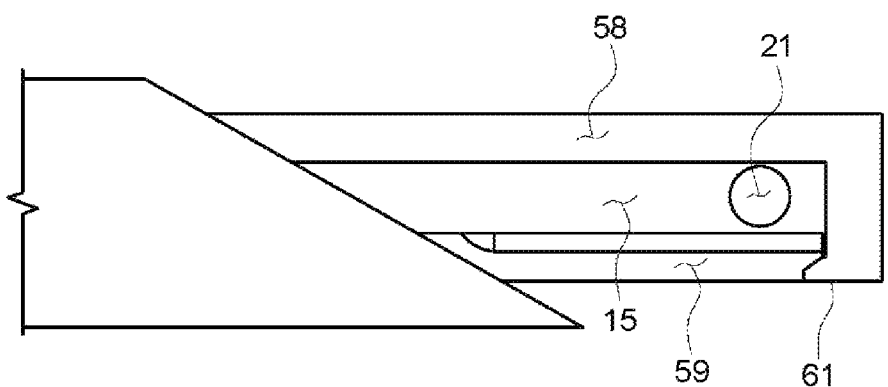

FIGS. 34 and 35 show variations with the short finger positioned as the lower finger. A simple butt joint 54 between the upper finger 58 and lower finger 59 form a slot 15 to capture suture 21 as shown in FIG. 34. In order to make the construct more stable, the two fingers can be temporarily held together using a tooth 61 on the upper finger 58 as shown in FIG. 35.

Any combination of the features noted in FIGS. 30-35 can be interchanged to create other finger designs.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Claim elements and steps herein may have been numbered and/or lettered solely as an aid in readability and understanding. Any such numbering and lettering in itself is not intended to and should not be taken to indicate the ordering of elements and/or steps in the claims.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a sub combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A medical instrument comprising:
   a handle;
   a hollow shaft extending from the handle;
   a set of fingers including a first finger and a second finger; and
   a slide disposed on the handle, the slide operably connected to the set of fingers to cause the set of fingers to extend from the hollow shaft, in a deployed configuration, and retract into the hollow shaft, in a retracted configuration, upon movement of the slide along the handle, wherein
   the first finger and the second finger separating from each other, resulting in an open configuration, as the set of fingers move from the retracted configuration to the deployed configuration;

the first finger and the second finger coming together, resulting in a closed configuration, at a joint as the set of fingers move from the deployed configuration to the retracted configuration; the slide operable to move the first finger and the second finger together longitudinally, from the retracted configuration and then the slide is operable to move the first finger longitudinally relative to the second finger; and the device including a locking structure to lock the first finger and the second finger in the closed configuration, preventing inadvertent separation between the first finger and the second finger.

2. The medical instrument of claim 1, wherein a slot is formed between the first finger and the second finger in the closed configuration.

3. The medical instrument of claim 2, wherein the slot has a width sufficient to permit a suture to slide therethrough when the set of fingers are in the closed configuration.

4. The medical instrument of claim 1, wherein the first finger is a short finger and the second finger is a hooked finger having a hook at a distal end thereof.

5. The medical instrument of claim 4, wherein the joint is formed from a distal end of the short finger and a handle-facing end of the hooked finger.

6. The medical instrument of claim 5, wherein the locking structure includes a short finger ledge disposed on the distal end of the short finger, the short finger ledge fitting into a hooked finger ledge to form the joint with at least a portion of the short finger ledge being within a space defined by a hook of the hooked finger.

7. The medical instrument of claim 5, further comprising a ram formed at the distal end of the short finger, the ram forming a hooked end slot defined by a distal surface of the ram and a hook of the hooked finger when in the closed configuration.

8. The medical instrument of claim 7, further comprising a ram extension fitting into the hooked end slot when in the closed configuration.

9. The medical instrument of claim 8, wherein the ram extension has a length sufficient to press against a suture disposed in the hooked end slot, preventing sliding of the suture within the hooked end slot.

10. The medical instrument of claim 1, wherein the first finger includes a tooth that meshes with a chamfer formed in the second finger, the tooth and chamfer forming the joint in the closed configuration.

11. The medical instrument of claim 1, wherein the slide includes a first slide, operable to move the first finger, and a second slide, operable to move the second finger.

12. The medical instrument of claim 1, wherein:
the slide is attached to the first finger;
a spring is configured to resiliently urge the second finger into the closed configuration with the first finger;
a stop limits extension of the second finger from the shaft, relative to the first finger, during movement into the deployed configuration, wherein
extension of the first finger by movement of the slide causes the first finger to separate from the second finger in the open configuration and the deployed configuration.

13. The medical instrument of claim 1, wherein the locking structure includes an inside diameter surface of the shaft.

14. A medical instrument comprising:
a handle;
a hollow shaft extending from the handle, the hollow shaft having a distal end with a sharpened tip;
a set of fingers including a first finger and a hooked finger having a hook at a hooked finger distal end thereof, a hook distal end surface of the hook facing the handle, a first finger distal end surface facing the hook distal end surface; and
a slide disposed on the handle, the slide operably connected to the set of fingers to cause the set of fingers to extend from the hollow shaft, in a deployed configuration, and retract into the hollow shaft, in a retracted configuration, upon movement of the slide along the handle, wherein
the first finger and the hooked finger separating from each other, resulting in an open configuration, as the set of fingers move from the retracted configuration to the deployed configuration;
slide operable to move the first finger and the hooked finger together longitudinally, from the retracted configuration and then the slide is operable to move the first finger longitudinally relative to the hooked finger;
the first finger and the hooked finger coming together, resulting in a closed configuration, at a joint as the set of fingers move from the deployed configuration to the retracted configuration; and
a slot is formed between the first finger and the hooked finger in the closed configuration.

15. The medical instrument of claim 14, wherein the first finger includes a tooth that meshes with a chamfer formed in the hooked finger, the tooth and chamfer forming the joint in the closed configuration.

16. The medical instrument of claim 14, wherein the slot has a width sufficient to permit a suture to slide therethrough when the set of fingers are in the closed configuration.

17. The medical instrument of claim 14, further comprising a ram formed at the first finger distal end, the ram forming a hooked end slot defined by a distal surface of the ram and the hook of the hooked finger when in the closed configuration.

18. The medical instrument of claim 17, further comprising a ram extension fitting into the hooked end slot when in the closed configuration, wherein the ram extension has a length sufficient to press against a suture disposed in the hooked end slot, preventing sliding of the suture within the hooked end slot.

19. The medical instrument of claim 14, wherein:
the slide moves the first finger and the hooked finger between the open and closed configurations via at least one of a first mechanism and a second mechanism;
the first mechanism includes a first slide, operable to move the first finger, and a second slide, operable to move the hooked finger; and
the second mechanism includes:
the slide being attached to the hooked finger;
a spring is configured to resiliently urged the first finger into the closed configuration with the hooked finger;
a stop limits extension of the first finger, relative to the hooked finger, from the shaft during movement into the deployed configuration; and
extension of the hooked finger by movement of the slide causes the first finger, whose extension is restricted by the stop, to separate from the hooked finger in the open configuration and the deployed configuration.

20. A medical instrument comprising:
a handle;
a hollow shaft extending from the handle, the hollow shaft having a distal end with a sharpened tip;

a set of fingers including a first finger and a hooked finger having a hook at a hooked finger distal end thereof, a hook distal end surface of the hook facing the handle, a first finger distal end surface facing the hook distal end surface; and a slide disposed on the handle, the slide operably connected to the set of fingers to cause the set of fingers to extend from the hollow shaft, in a deployed configuration, and retract into the hollow shaft, in a retracted configuration, upon movement of the slide along the handle, wherein the first finger and the hooked finger separating from each other, resulting in an open configuration, as the set of fingers move from the retracted configuration to the deployed configuration;

the first finger and the hooked finger coming together, resulting in a closed configuration, at a joint as the set of fingers move from the deployed configuration to the retracted configuration; the slide operable to move the first finger and the hooked finger together longitudinally, from the retracted configuration and then the slide is operable to move the first finger longitudinally relative to the hooked finger;

the medical instrument including a locking structure to lock the first finger and the hooked finger in the closed configuration, preventing inadvertent separation between the first finger and the hooked finger; and a slot is formed between the first finger and the hooked finger in the closed configuration, where a suture is operable to slide along the slot.

21. The medical instrument of claim 20, wherein the locking structure includes at least one of (1) a latching mechanism between the hooked finger and first finger or (2) an inside diameter surface of the shaft.

* * * * *